(12) United States Patent
Dillon et al.

(10) Patent No.: US 6,540,696 B1
(45) Date of Patent: Apr. 1, 2003

(54) GUARDING NEEDLES IN IV PROCEDURES

(75) Inventors: Jagmohanbir Singh Dillon, Act (AU);
William Leonard Mobbs, Act (AU)

(73) Assignee: Noble House Group Pty. Ltd.

( * ) Notice: Subject to any disclaimer, the term of this patent is extended or adjusted under 35 U.S.C. 154(b) by 0 days.

(21) Appl. No.: 09/720,053

(22) PCT Filed: Jul. 23, 1999

(86) PCT No.: PCT/AU99/00598

§ 371 (c)(1),
(2), (4) Date: Dec. 20, 2000

(87) PCT Pub. No.: WO00/06225

PCT Pub. Date: Feb. 10, 2000

(30) Foreign Application Priority Data

| Oct. 16, 1998 | (AU) | PP6597 |
| Sep. 4, 1998 | (AU) | PP5722 |
| Jul. 24, 1998 | (AU) | PP4869 |

(51) Int. Cl.[7] .................................................. A61B 5/00
(52) U.S. Cl. ........................................ 600/573; 604/187
(58) Field of Search ................................ 600/573–583; 604/187–207, 403–416

(56) References Cited

U.S. PATENT DOCUMENTS

| 4,449,539 A | 5/1984 | Sarstedt |
| 4,784,650 A | 11/1988 | Coburn |
| 4,932,418 A | 6/1990 | Coburn |
| 5,030,209 A | 7/1991 | Wanderer et al. |
| 5,112,311 A | 5/1992 | Utterberg et al. |
| 5,259,392 A | 11/1993 | Schmitt |
| 5,752,936 A | 5/1998 | Chen |
| 5,782,820 A | 7/1998 | Roland |

FOREIGN PATENT DOCUMENTS

| AU | 654464 | 11/1994 |
| AU | 695517 | 11/1995 |
| DE | 42 22 398 | 1/1994 |
| EP | 587 347 | 3/1994 |
| WO | WO 88/05286 | 7/1988 |

*Primary Examiner*—Max F. Hindenburg
*Assistant Examiner*—Pamela L Wingood
(74) *Attorney, Agent, or Firm*—Sidley Austin Brown & Wood LLP

(57) ABSTRACT

A method and apparatus are disclosed for guarding both the IV needle and the sampling port needle in IV procedures, whereby the opening end of a needle guard containing an IV needle is inserted into the open end of a tubular sampling port so that the sampling port needle enters the guard. The guard may be provided with a catch that engages a corresponding aperture in the port when the guard is fully inserted into the port so that the guard is retained within the port against inadvertent removal.

24 Claims, 9 Drawing Sheets

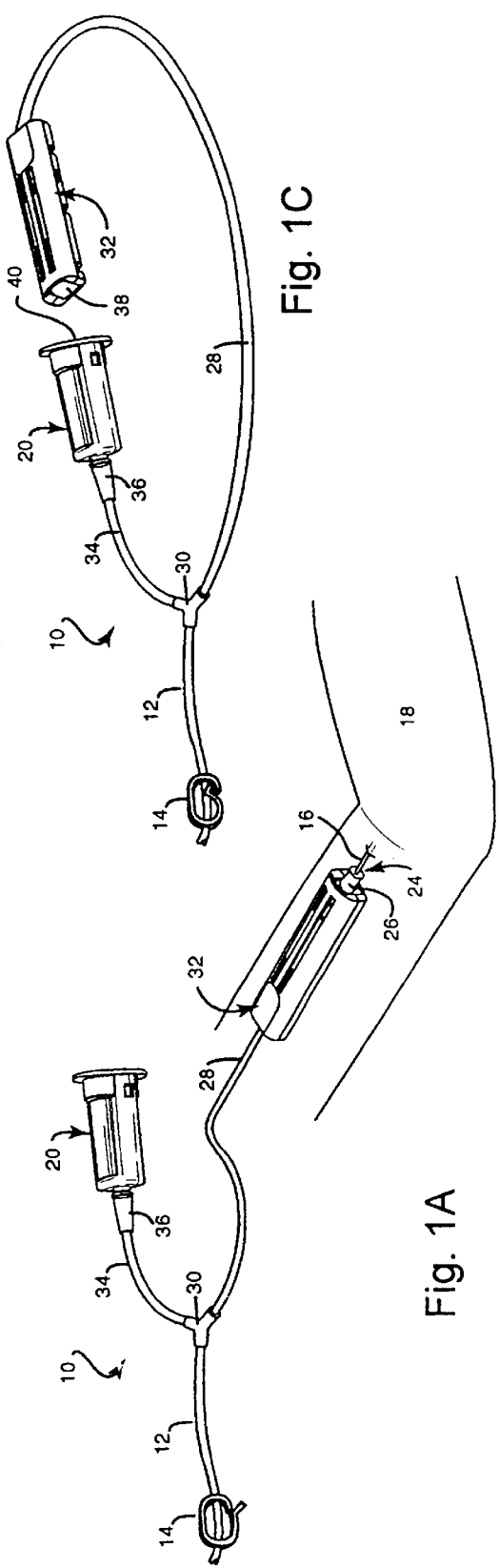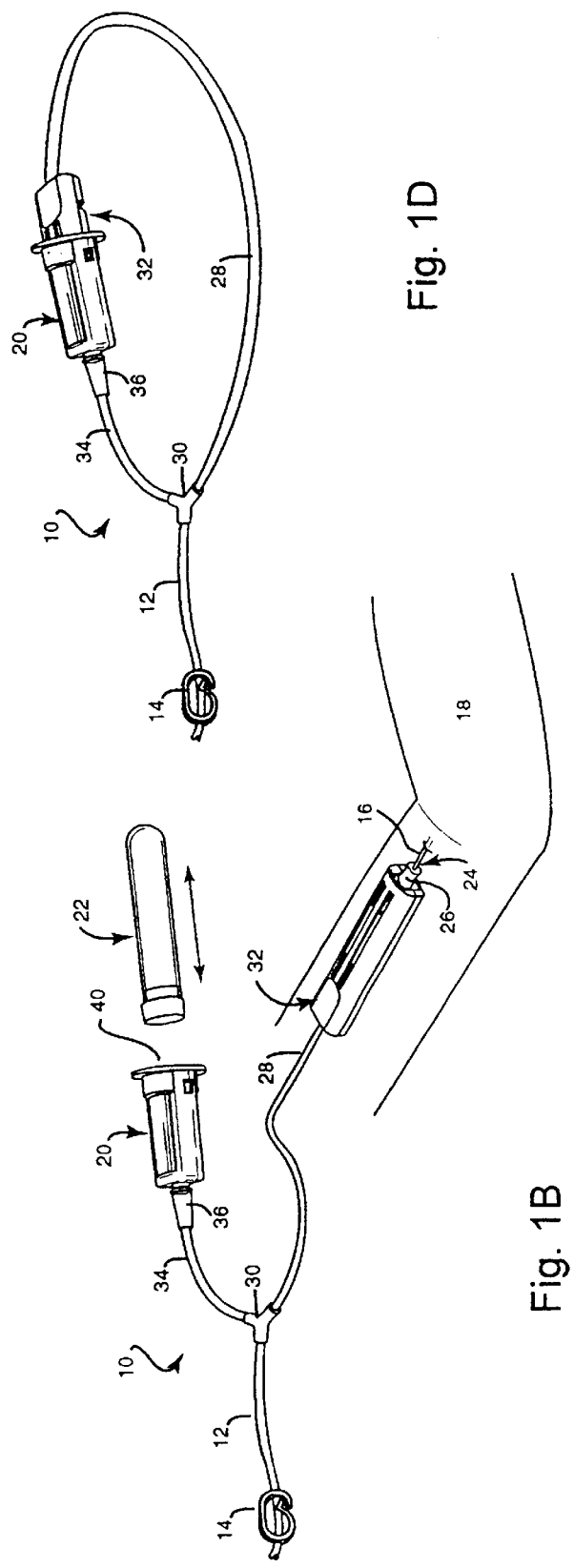

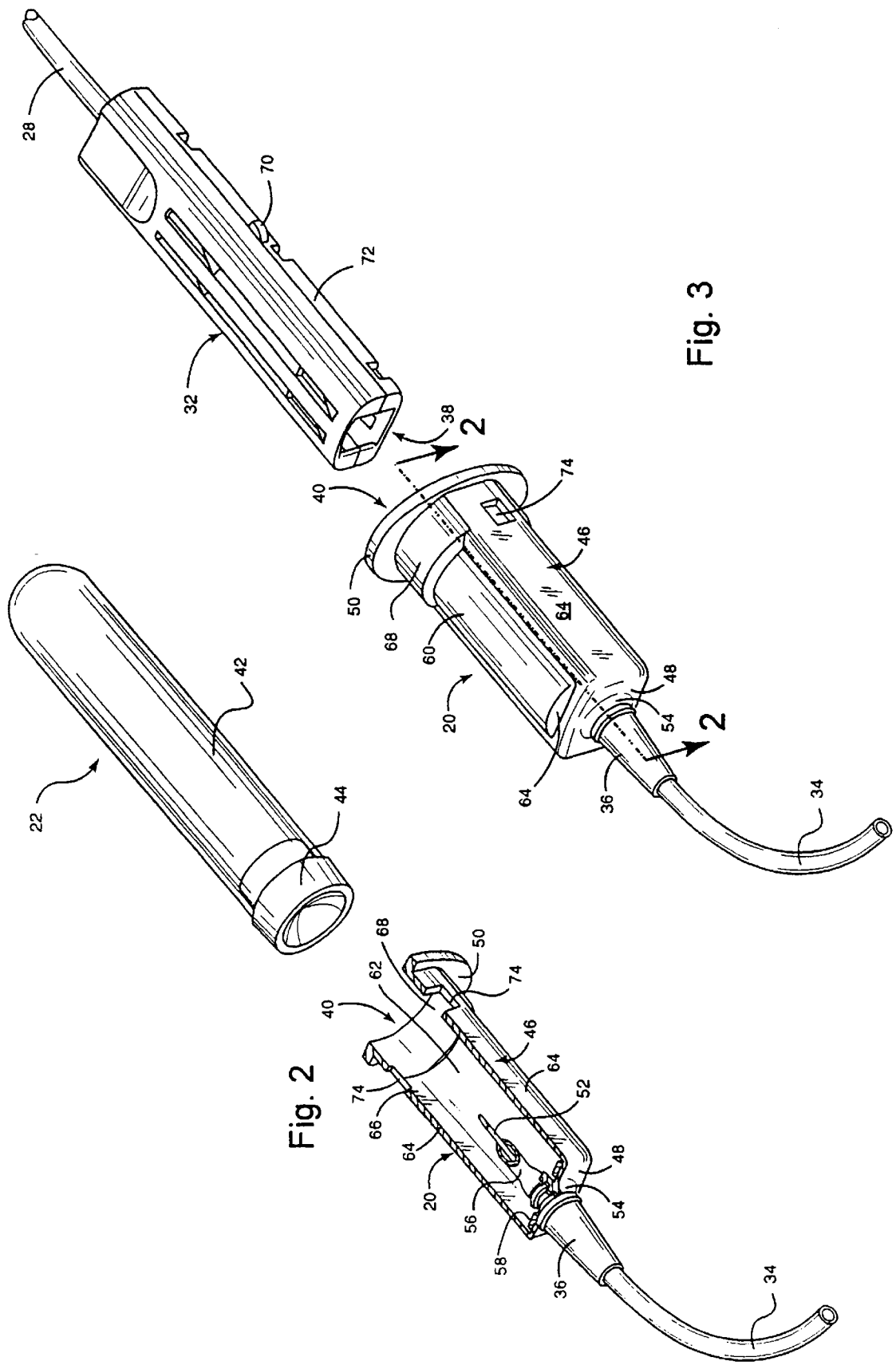

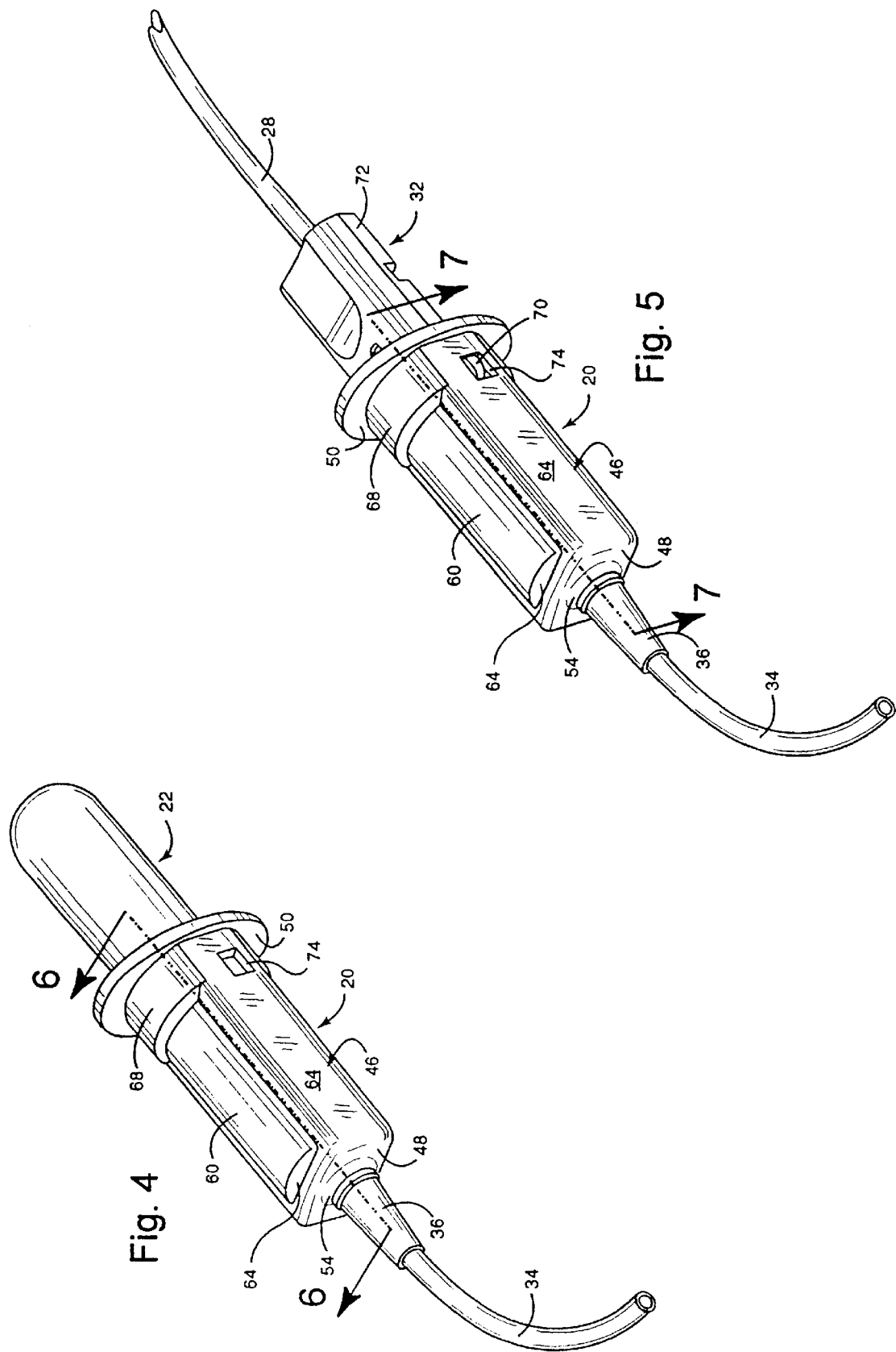

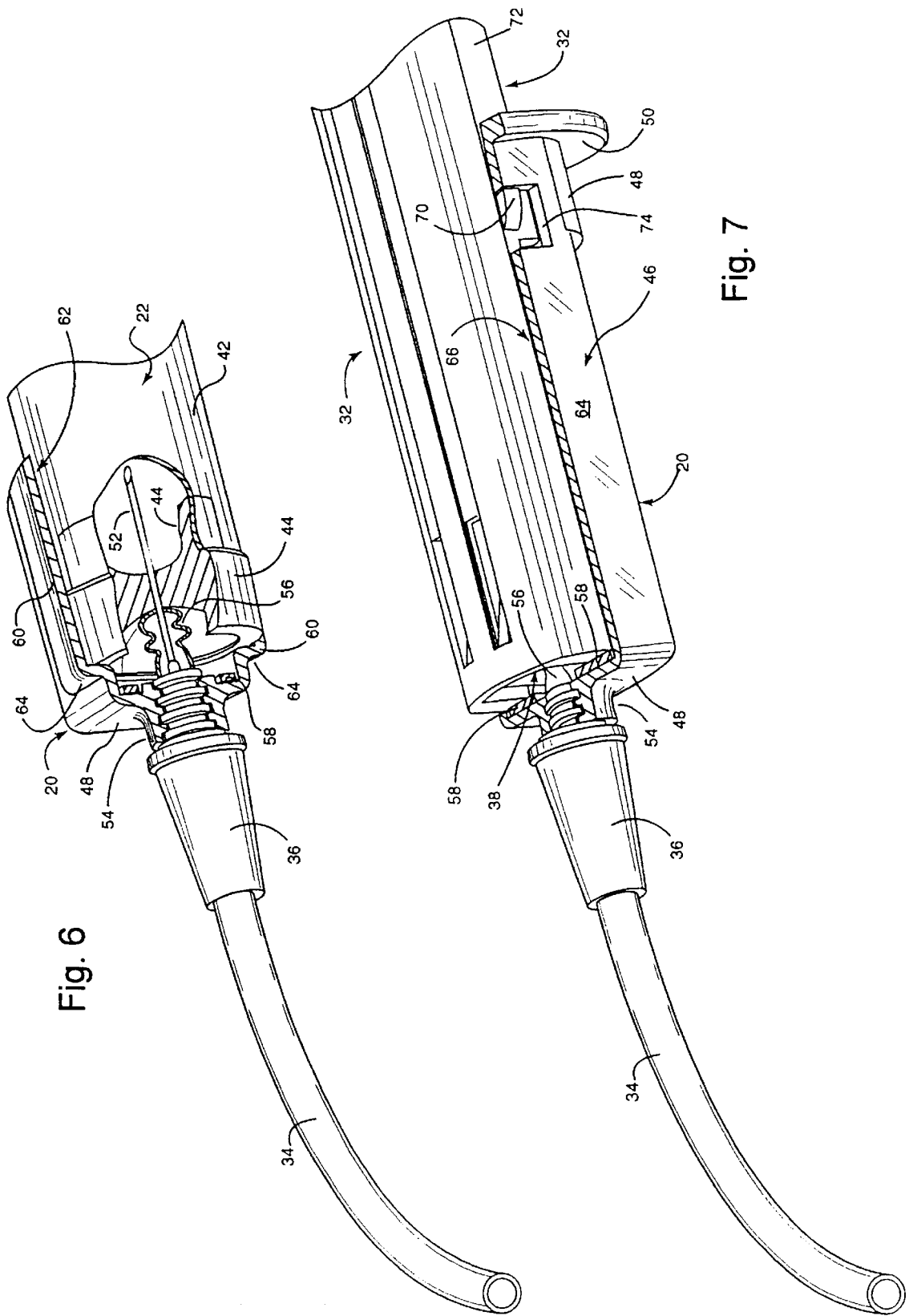

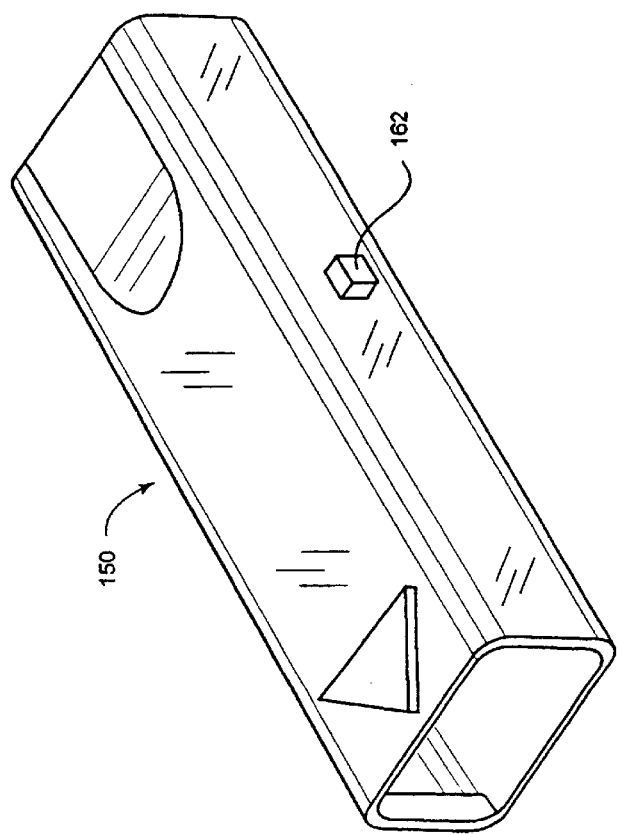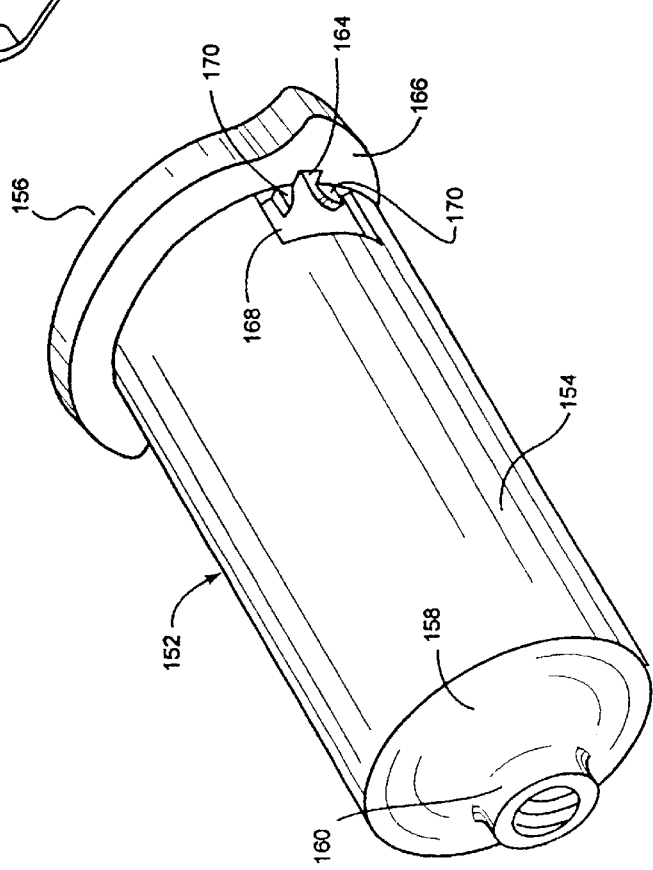
Fig. 11

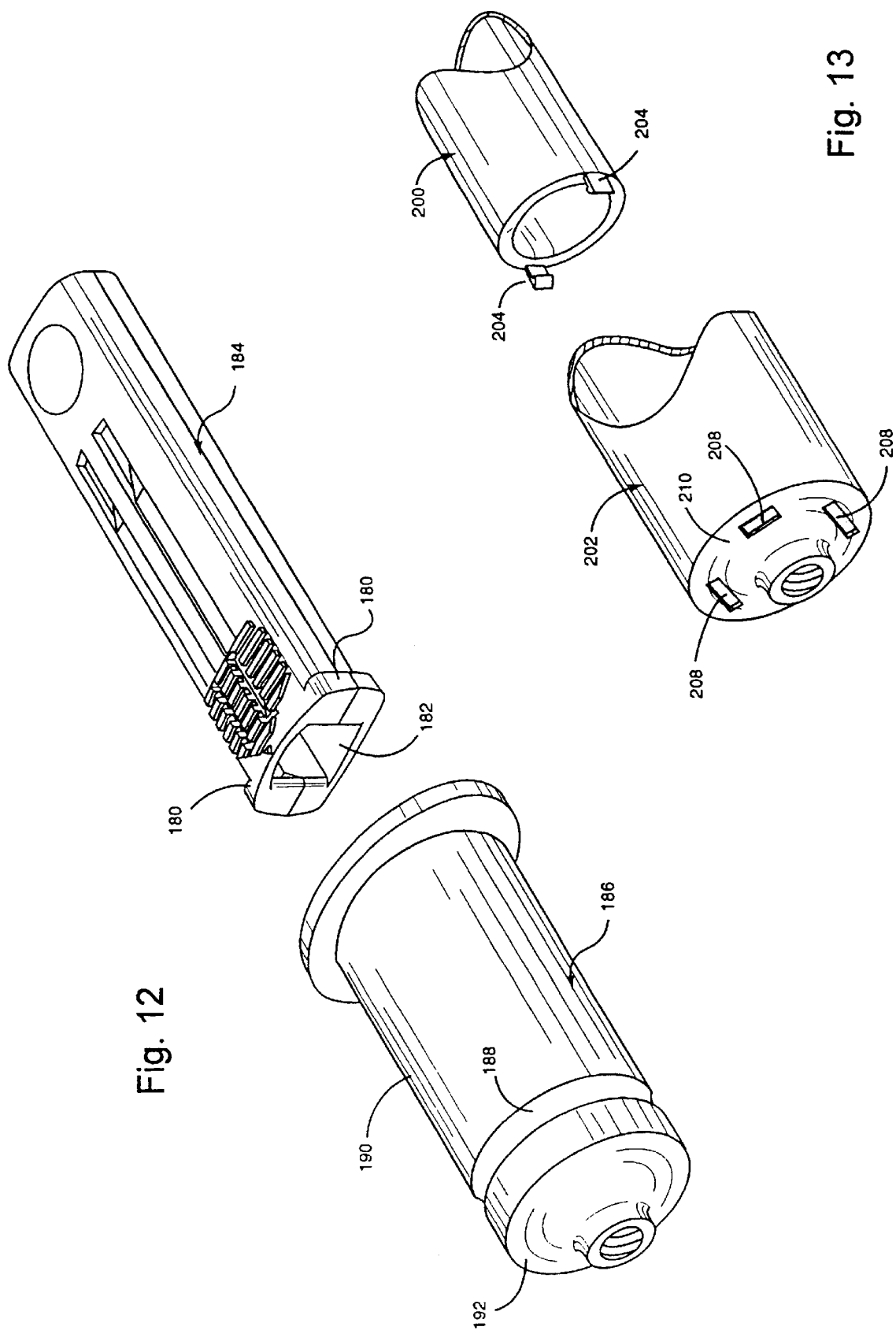

GUARDING NEEDLES IN IV PROCEDURES

TECHNICAL FIELD

This invention relates to methods and apparatus for mitigating the danger of needle-stick and blood-splash during intravenous (IV) and similar medical procedures where a first needle is used to access a blood vessel and a second needle is used in a sampling port to draw-off samples of liquid obtained from the patient or delivered to the patient. The most common use envisaged for such methods and apparatus is in blood collection from blood donors, but the invention is also applicable to other intravenous medical procedures such as renal dialysis and the sampling of liquids from body cavities. The invention is also concerned with the design and use of sampling ports and needle guards employed in any such procedure.

In this specification, 'needle-stick' refers to the pricking of a phlebotomist or other person with a used needle, while 'blood-splash' refers to the dripping or oozing of blood or other body liquid from a needle onto a person, or onto a surface that could come into contact with a person.

For convenience, this invention will be described with particular reference to procedures for collecting blood from donors but it will be appreciated that the invention is not necessarily confined to this context. Also for convenience, a sampling port may simply be referred to as a 'port'.

BACKGROUND

The collection of blood from donors, along with other IV procedures, involves the use of a needle assembly comprising a hypodermic needle that is connected to a flexible trailing tube via a needle hub. For convenience such needle assemblies may be referred to as IV needle assemblies.

Our prior Australian patent Nos 654464 and 695517 disclose a needle guard suitable for use with blood collection procedures employing IV needle assemblies. This guard is placed on the trailing tube so that the needle can be withdrawn from a patient directly into the guard by pulling on the tube. Once fully withdrawn into to guard, the needle is automatically locked within the guard so that it cannot be removed and so that it is rendered safe against needle-stick for handling and disposal. However, blood-splash can still occur through the open end of a guard housing a used needle. It is also known to form a needle guard around the needle and hub of an IV needle assembly so that the guard is permanently attached to the needle assembly. In such guards, the unused needle can be extended from the guard for use and withdrawn into to guard after use but, again, there is the danger of blood-splash from the open end of a guard containing a used needle.

Since samples of blood must be taken for analysis at the time of blood collection, it is common practice to connect a sampling port to the trailing tube of the needle assembly and to dispose of the sampling port, needle and interconnecting tubing as a single item after use. The common port is simply a hollow moulded-plastic cylinder or barrel that has a closed base and an open top. A hollow needle is mounted in the base so that it extends axially into the barrel, the butt of the needle being connected externally of the port to the trailing tube of the needle assembly. A rubber-like sheath normally covers the port needle. To collect a blood sample, a sealed vacuum phial with a rubber-like bung is pushed into the port and onto the sheathed needle so that the port needle penetrates its sheath and the bung, causing blood (or other liquid) to be sucked into the phial from the tube of the needle assembly. When the phial is pulled out of the port, the needle is extracted from the bung, the bung reseals and the sheath springs back to cover the needle again.

While the barrel of the port is intended to shield the user from contact with the port needle, a user can inadvertently put a finger into the port and suffer needle-stick injury. It is also possible for blood to be exuded from the port needle and result in blood-splash contamination through the open end of the port. This can happen in various ways: blood can ooze through the pierced end of the sheath; the sheath may not spring back and re-cover the needle allowing blood to flow from the needle point; if more than one sample is taken, compression of the sheath by each phial after the first will force blood from the bottom of the sheath into the base of the port.

To address the danger of blood-splash from the open end of a needle guard or a sampling port, and to mitigate the danger of needle-stick from the port needle, it is known to provide push-on caps for each type of device. An example of the use of a push-on cap for a needle guard is provided by Utterberg in U.S. Pat. No. 5,112,311 and examples of the use of push-on caps for ports are provided by Coburn in U.S. Pat. Nos. 4,784,650 and 4,932,418, Chen in U.S. Pat. No. 5,752,936, Schmitt in U.S. Pat. No. 5,259,392. and Broden in WO 88/05286. While effective, the use of such caps is bothersome and time-consuming for a phlebotomist.

Another known approach to mitigation of blood-splash from needle guards relies upon the use of textured surfaces or adsorbent pads in the guards near their open ends. This is exemplified by the above mentioned Utterberg patent and our Australian patents 654464 and 695517. Similarly, to inhibit blood forced from the bottom of a port-needle sheath from oozing along the screw-thread by which the butt end of a sampling port needle is mounted in the base of the port, U.S. Pat. No. 5,782,820 to Roland discloses the use of an adsorbent washer between the flange of the threaded needle butt and the exterior of the base of the port. Such a washer does not, however, mitigate blood-splash from the open end of the port, which is the principal danger.

OBJECTIVES OF THE INVENTION

The invention seeks to provide means for mitigating the danger of blood-splash contamination the open end of a guarded IV needle and/or from the open end of a sampling port.

OUTLINE OF THE INVENTION

From one aspect, the present invention comprises a method of mitigating the danger of blood-splash contamination from the open end of a needle guard and/or from the open end of a sampling port, the method involving inserting the open end of the needle guard into the open end of the port. Preferably, the guard is inserted so that the port needle enters the open end of the guard. The method may also include the steps of connecting the port-needle to the trailing tube of the needle assembly, taking samples from the trailing tube using vacuum phials, withdrawing the IV needle into its guard, inserting the guard into the open end of the port and/or securing the needle guard in the port against unintended removal.

From another aspect, the invention may comprise a tubular needle guard having retaining means adapted to retain the guard within a sampling port when the guard is inserted into the port open-end first. Similarly, the invention may comprise a tubular port having retaining means adapted to retain a tubular needle guard that has been inserted into the port open-end. The retaining means may comprise clips, catches, barbs or the like that are engaged by simply pushing the guard into the port, but twisting or turning the guard in the port to effect retention is also envisaged.

An adsorbent pad of material may be incorporated in the closed base of the port around the butt of the port needle and the guard may be entered into the port so that the open end of the guard is close to or presses upon the pad to reduce the likelihood that blood will find its way from the open end of the guard into the barrel of the port. In this way, substantially the full length of the port needle may be inserted into the guard and the open end of the guard may be substantially closed by the base of the port or by a pad therein. In addition to or instead of the pad, the interior of the base of the port may be coated or treated to promote the immobilisation and/or rapid clotting of blood.

It is desirable that separate guide means are formed in the barrel of the sampling port to accommodate and guide a phial and a guard during insertion into the port, at least the guide means for the phial including stop means that limits the inward travel of the phial into the port. This enables the limit for phial penetration to be set so that the bung of the phial cannot contact the base of the port or an adsorbent pad fitted in the base, since such contact may contaminate the end of the bung with blood or other liquid on the pad or base of the port. On the other hand, the use of separate guide and/or stop means allows a guard to be entered further into the port than a phial, permitting the end of the guard to be positioned in contact with or in close proximity to the base of the port or a pad fitted therein. It is also desirable to limit the penetration of a phial into the port to ensure that the needle sheath is not damaged by excessive compression.

Conveniently, the guard can have a generally rectangular section and the phial a smaller generally circular section, and the guide means can comprise grooves or channels formed in the wall of the barrel of the port that are shaped and dimensioned so that phials and guards are guided and stopped differently.

The materials employed for the port pad can be fibrous or foamed, synthetic and/or natural, so long as they are highly wettable and capable of rapidly absorbing and retaining substantial quantities of aqueous liquids (in relation to their dry weight or volume). Examples of suitable materials are cellulose fibres (natural or synthetic), plasters, clays, fired or unfired but unglazed ceramic materials, foamed materials of synthetic or natural components. Such materials may be formed into washer-like discs and pressed and/or glued into the base of the sampling port so that they are retained therein. If desired, the internal surface of the port and/or the external surface of the internal needle boss can include a recess or ridge to assist in retaining the discs.

Suitable coatings can be formed from a variety of natural or synthetic materials applied as paints or slips which dry to form porous and/or hydrophilic layers on the interior of the sampling port, preferably at or near the base thereof.

The treatments envisaged include the formation of etched or textured surfaces on the interior of the sampling ports, preferably near their closed ends were first contact with blood or other fluid which has leaked from the port needle is most likely. The etching may be effected by acid etching the exterior of the core used in moulding the port, or it may be effected by treating the interior of the port with acids, plasma discharges or the like.

The pad materials and/or the interior of the port may be impregnated, coated or otherwise treated with fine particulate minerals, such as the silicates of, sodium, potassium, magnesium and/or aluminium, titanium dioxide, diatomaceous earth. Fine powders of fired or unfired clays, cementicous materials or the like may also be employed. Preferably, such mineraliferous materials have particle sizes of less than 20 $\mu$, more preferably less than 5 $\mu$ and most preferably of sub-micron dimensions (ie, less than 1 $\mu$). As an alternative—or in addition—to the use of mineraliferous materials, this invention also envisages the use of intrinsic clotting pathways. For example, the pads may incorporate thrombin, heparinase and/or fibrinogen, or various peptides and proteins.

DESCRIPTION OF EXAMPLES

Having broadly portrayed the nature of the present invention, exemplary embodiments will now be described with reference to the accompanying drawings, in which:

FIG. 1A is a diagram showing an IV needle assembly, guard, sampling port and phial being used to collect blood.

FIG. 1B is a diagram showing the system of FIG. 1A being used to collect blood samples.

FIG. 1C is a diagram showing the system of FIG. 1A after collection of samples and withdrawal of the IV needle guard into the sampling port.

FIG. 1D is a diagram of the system of FIG. 1A after the needle guard has been inserted into the sampling port.

FIG. 2 is an enlarged perspective view of the sampling port employed in the system of FIGS. 1A–1D, showing a sampling phial aligned therewith, the sampling port being shown in longitudinal section taken on plane 2—2 of FIG. 3.

FIG. 3 is an enlarged perspective view of the sampling port and an aligned needle guard of the system of FIGS. 1A–1D.

FIG. 4 is an enlarged perspective view of the sampling port and phial of the system of FIGS. 1A–1D, with the phial fully inserted in the port.

FIG. 5 is an enlarged perspective of the port of FIGS. 1A–1D with the needle guard fully inserted therein.

FIG. 6 is an enlarged longitudinal section of portion of the port and phial of FIG. 4 taken on section plane 6—6 of FIG. 4.

FIG. 7 is an enlarged longitudinal section of portion of the port and guard of FIG. 5 taken on section plane 7—7 of FIG. 5.

FIG. 11 is a perspective view of a sampling port and guard, which comprise a third example of a guard and port combination, but with both the needle assembly and the port-needle omitted for clarity.

FIG. 12 is a perspective of the of a sampling port and guard, which comprise a fourth example of a guard and port combination; with both the needle assembly and the port-needle omitted for clarity.

FIG. 13 is a perspective view of portions of a sampling port and guard, which comprise a fifth example of a guard and port combination, but with both the needle assembly and the port-needle omitted for clarity.

Figure 8:
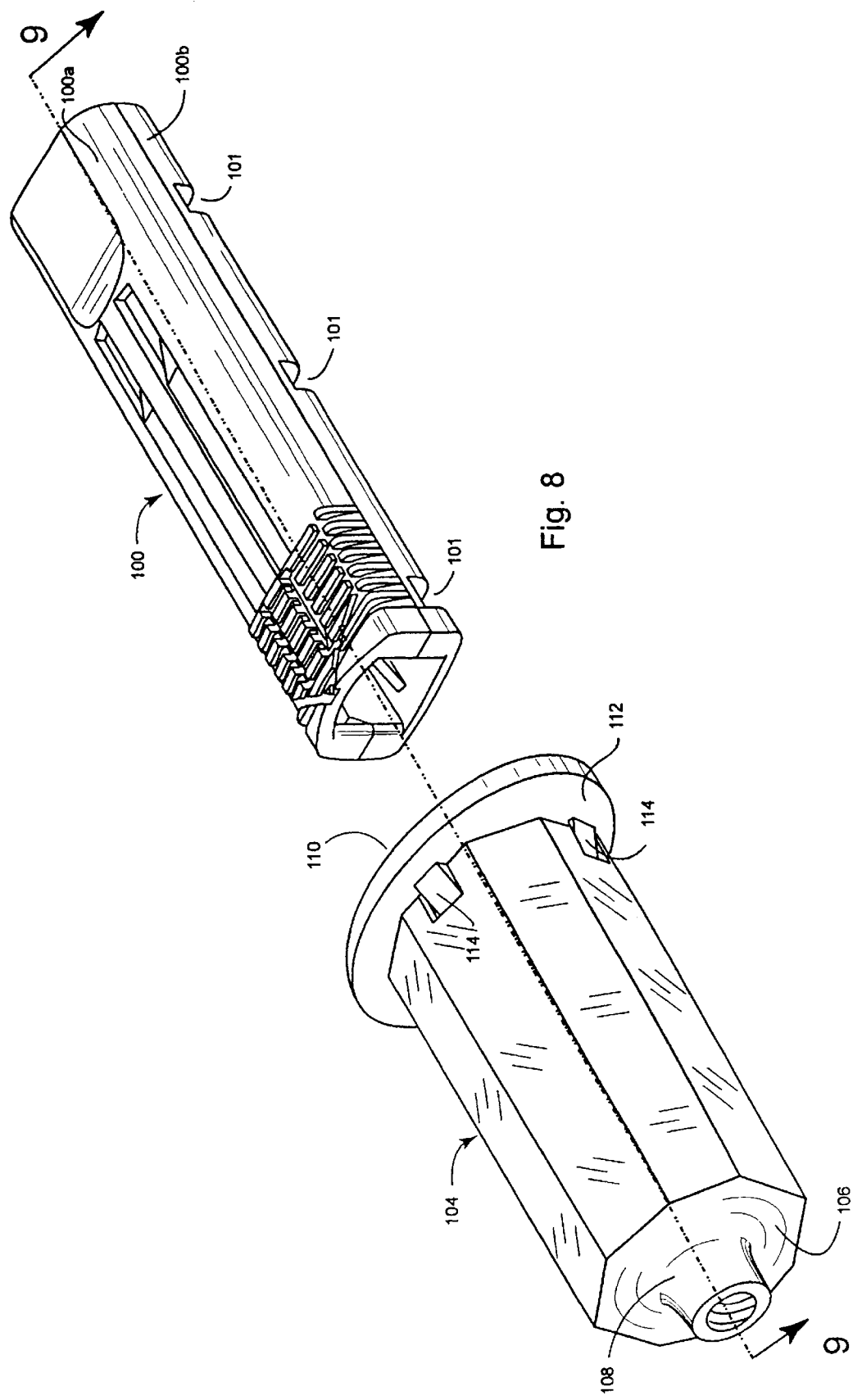
FIG. 8 is a perspective view of a second example of a guard and port combination showing the guard aligned with the port, but with both the needle assembly and the port-needle omitted for clarity.

A system 10 for collecting blood and blood samples from blood donors is shown in FIGS. 1A–1D. FIG. 1A shows the blood collection under-way; that is, blood is flowing in the blood-line 12 to collection bags (not shown), cut-off clamp 14 being open and the needle 16 remaining the donor's arm 18. FIG. 1B shows system 10 when blood collection has been completed, clamp 14 is closed to seal blood-line and, preferably, blood-line 12 is severed immediately downstream of clamp 14. Samples can now be drawn off using a sampling port 20 and vacuum phials 22 without any fear of contaminating the collected blood.

In this example, the needle assembly 24, comprises the needle 16, a needle hub 26 and a trailing tube 28 that is connected to a Y-joint 30 which is, in turn, connected to blood-line 12. A needle guard 32 of the type that slides on trailing tube 28 is shown partially covering needle hub 26, but it will be appreciated that guard 32 can be of the type that does not slide on tube 28 but completely encloses and permanently captures needle hub 26. Sampling port 20 is shown connected to Y-joint 30 by a sampling tube 34, but tube 34 can be dispensed with if spigot 36 extending from the base of port 20 can be inserted directly through a membrane or valve seal into joint 30. Normally, spigot 36 is formed by the butt end of the port-needle (to be described below).

After sufficient samples have been collected, needle 16 is withdrawn from arm 18 directly into guard 32 by pulling on trailing tube 28 while holding the guard, needle 16 and hub 26 being automatically locked inside guard 32 so that the point of needle 16 is not accessible. Immediately after withdrawal of needle 16 into guard 32, the guard is held in one hand by the phlebotomist and turned so that its open end 38 is aligned with the open top 40 of port 20, which is held in the phlebotomist's other hand. At this point, system 10 is as shown in FIG. 1C and, in partial enlargement, in FIG. 3. Finally, guard 32 (with needle 16 encased therein) is pushed home into port 20 and needle assembly 24, guard 32 and port 20 (with associated tubes 28, 34 and (portion of) 12, together with Y-joint 30) are disposed of in a bag (not shown) for contaminated waste. The situation immediately prior to disposal is shown in FIG. 1D and in partial enlargement in FIG. 5.

FIGS. 2, 4 and 6 illustrate the port 20 and phial 22 in greater detail, FIG. 2 showing phial 22 as it is about to be inserted in port 20, FIG. 4 showing phial 22 fully inserted in port 20 and FIG. 6 being a partial longitudinal section of the fully-inserted phial. Phial 22 is a standard and well-known product, having a transparent glass or plastic test-tube like body 42 fitted with a pierceable rubber-like bung 44 and being evacuated. Sampling port 20 has an elongate barrel-like body 46 with open top 40 and a closed base 48, the top 42 having an outwardly extending flange 50. Spigot 36 extends outwardly from base 48 to connect with sampling tube 34, spigot 36 being moulded onto the butt end of the port needle 52 and being screwed into an internally threaded boss 54 (see particularly FIG. 6) formed in the centre of base 48. Port-needle 52 is encased in a rubber sheath 56, shown extended but with its top cut away in FIG. 2 and shown compressed and in section in FIG. 6. An adsorbent pad 58 is located in the bottom of port 20 on the inner surface of base 48 so as to surround the bottom of needle 52 and sheath 56.

The barrel 46 of port 20 has opposed semi-cylindrical longitudinally-extending wall portions 60 that, internally, form guide channels 62 (FIG. 2) for guiding phials 22 as the phials are inserted into and withdrawn from port 20. Wall portions 60 and phial-guides 62 terminate in shoulders 64 near base 48 that serve to limit the penetration of a phial into the port so that the bung 44 cannot contact pad 58. (See FIG. 6).

FIGS. 3, 5 and 7 illustrate the interaction of guard 32 and port 20 in more detail. [This guard is substantially as disclosed in our aforementioned patents and reference to those patents should be made with regard to its function in relation to needle assembly 24.] Opposing sides of port barrel 46 form a pair of flat longitudinally extending wall portions 64 running substantially the full length of barrel 46, flats 64 being arranged in quadrature to cylindrical portions 60 of the barrel. Internally, wall portions 64 form a pair of opposed rectilinear grooves or guard-guide channels 66 (FIGS. 2 and 7) which, between them, are adapted to slidingly guide and accommodate the needle guard 32. The distance between opposing guard-guides 66 is greater than that between opposing phial-guides 62, so that guard 32 cannot enter or be guided by phial guides 62. However, to assist initial entry of guard 32 into port 20, the upper portion of barrel 46 is diametrically enlarged, as indicated at 68. This allows guard 32 to be inserted into enlargement 68 via port end 40 in any orientation and then rotated about its longitudinal axis to align guard 32 with guard-guides 66. It should be noted that the circumferential width of guard channels 66 is insufficient to allow phials 22 to enter them or to be guided by them. Thus, by means of guides 66, a guard 32 can be fully entered into port 20 so that its open end 38 contacts pad 58 at the bottom of the port (see FIG. 7), but a phial 22 cannot be entered so far into port 20 because its travel is limited by abutment of its bung 44 with shoulders 64 on phial-guides 62. This prevents bungs 44 of phials 22 from contacting pad 58 and being contaminated by blood in or on the pad.

In this first example, the retaining means that retain guard 32 in port 20 simply comprise a tooth-like catch 70 on at least one of the narrow sides 72 of guard 32, catch 70 being adapted to enter a corresponding aperture 74 near the top of either guard-channel 66 of port 20. While catches 70 may be formed on both sides of guard 34, moulding considerations associated with the particular guard disclosed in our above mentioned Australian patents, make it convenient to employ only one catch and to place that catch on the side of the guard that is not hinged. Since apertures 74 are formed on each side of port 20, guard 32 will be retained in the 20 in either of the ways it can be oriented in guide channels 66. It will be appreciated that essentially the same form of retaining means would result if internally facing tooth-like catches were formed on the inside of guard channels 66 and corresponding apertures were formed in the sides of guard 32, and that modification (among others) is envisaged by this invention. It will also be appreciated that the walls of guard 32 are sufficiently flexible so that they will deflect to allow catches 70 to enter port 20 and that barrel wall 46 of port 20 is sufficiently stiff so that, once catches 70 have engaged apertures 74, it will not be easy to squeeze cylindrical guide portions 60 together between the fingers sufficiently to release catches 70 from apertures 74.

Adsorbent pad 58 (FIGS. 2, 6 and 7) is shaped to fit the bottom of base 48 of port 20, which in this example is generally rectangular (see FIGS. 2–5), the pad having a central hole that fits closely around the butt 36 and sheath 56 of port needle 52. Pad 58 may be glued in place or held in place by friction. If desired, protrusions (not shown) may be formed on the inside of barrel 46 near base 48 to retain pad 58 in position. Pad 58 can be formed from highly porous cellulose material not unlike blotting paper and treated with sub-micron particles of $TiO_2$ and/or clay, the particles adhering to individual fibres rather than creating a filling or size that reduces the porosity of the pad. In addition to or instead of pad 58, the internal surfaces of port 20 near base 48 can be coated or treated with materials known to promote blood-clotting or to assist in immobilising the flow of blood or other aqueous liquids on or along surfaces. A simple treatment may be effected by etching the surface of the internal mould from which port 20 is formed, or by the use of plasma discharge within port 20. Some coatings that may be used have already been indicated in the Outline of Invention above.

Figure 9:
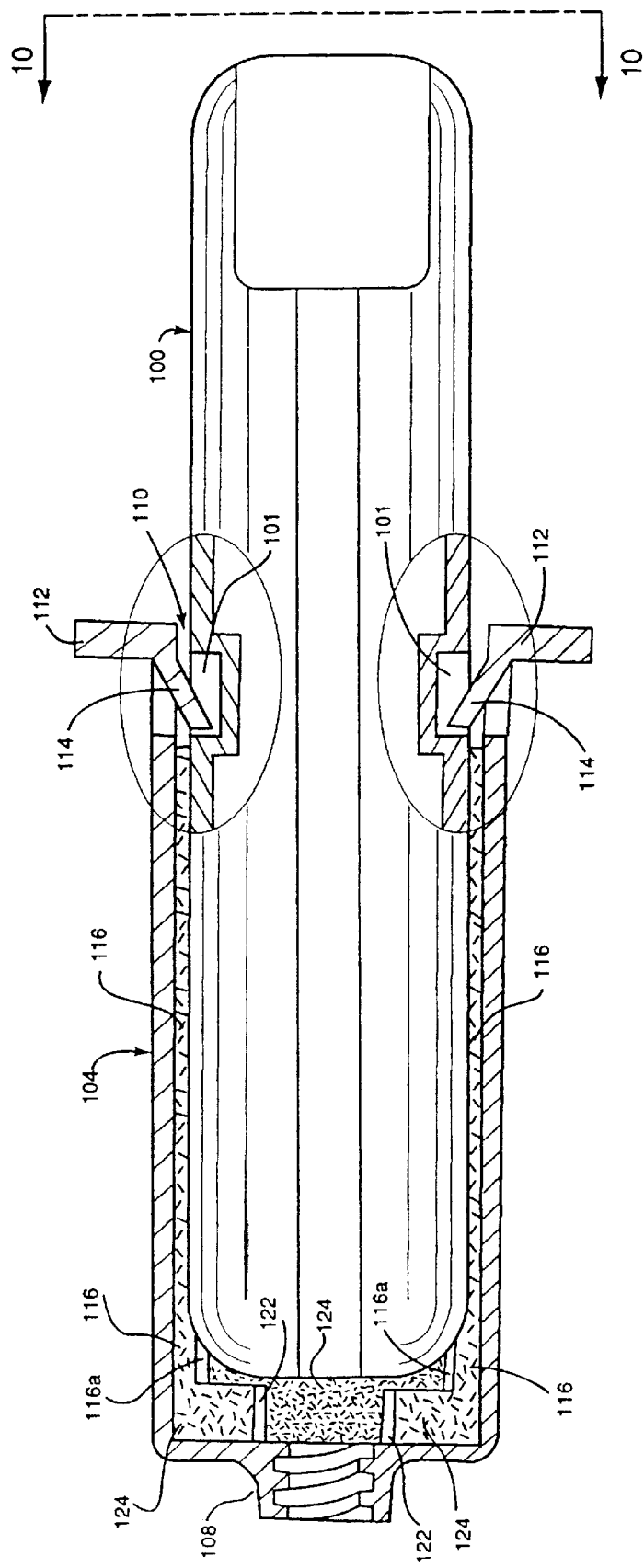
FIG. 9 is a sectional view, taken on plane 9—9, of the port of FIG. 8 with the guard of FIG. 8 fully inserted into the port.

The second example of the present invention shown in FIGS. 8 and 9 illustrates the use of an alternative form of retaining means to that of the first example, the needle guard 100 of this example being essentially the same as that (32) of the first example except that it does not have tooth-like catch 70 of that example. Guard 100 can be formed by clipping together two similar sub-members 100a and 100b, each having three side recesses 101 on one of their narrow side faces 102 to take corresponding clips (not shown here) on the other narrow side face of the other sub-member, the engagement of the clips and recesses 101 holding the sub-members together. In this example, sampling port 104 is also of tubular form, but of octagonal section, having a base 106 that has a central internally-threaded boss 108 adapted to take the threaded spigot of a sampling-port needle (not shown). As in the first example, port 104 has an open top 110 surrounded by a flange 112. Immediately below flange 112 are formed four evenly spaced inwardly facing resilient catches 114 that are adapted to enter any one of recesses 101 of a guard 100 that is inserted into port 102. Thus, in this example, recesses 101 and catches 114 form the retaining means. Preferably, as shown in FIG. 9, the guard is fully inserted into port 104 and the port is so dimensioned that one of catches 114 can enter the central one of recesses 101 when the guard is so inserted.

Figure 10B:
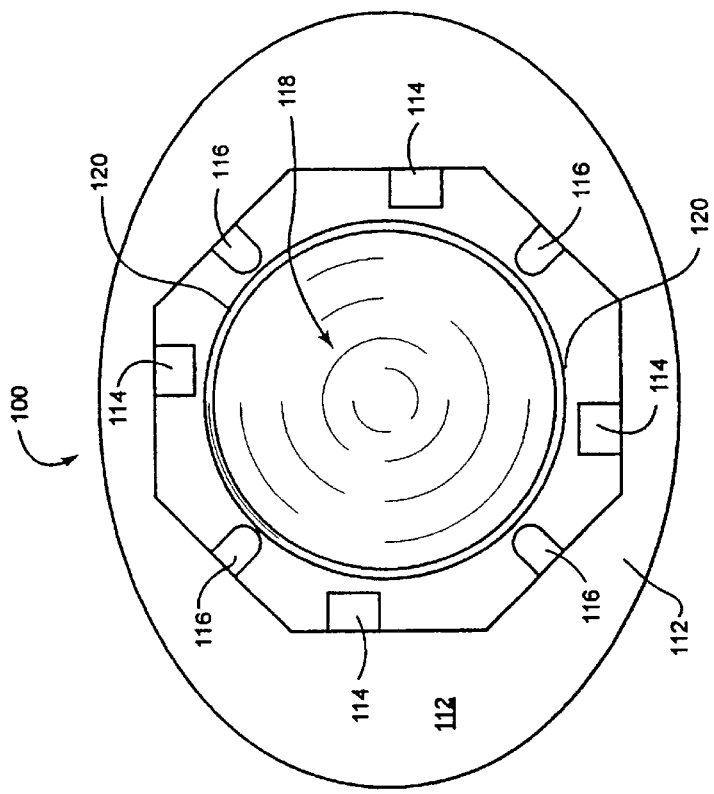
FIG. 10B is an end view of the port of FIG. 9 taken on plane 10—10 of FIG. 9, with a phial substituted for the guard of FIG. 10A.
Figure 10A:
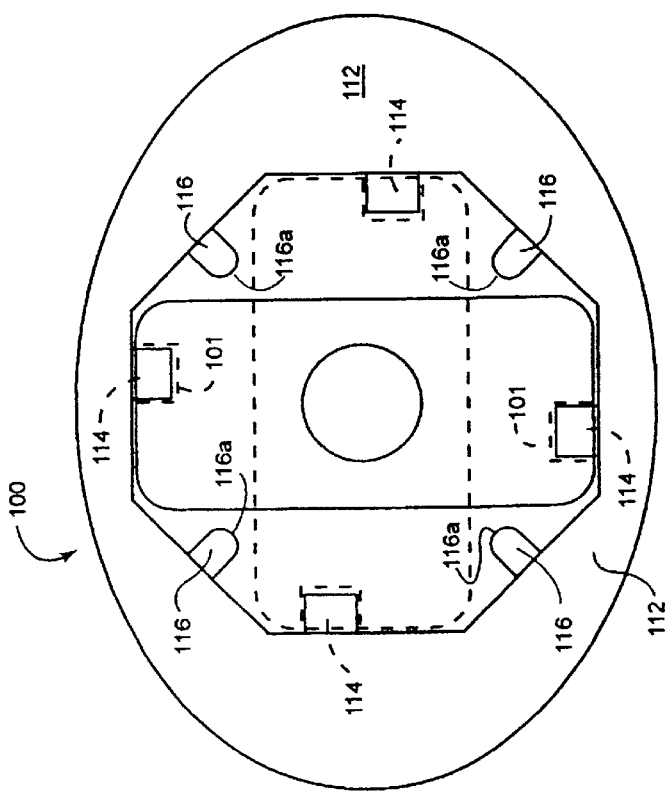
FIG. 10A is an end view of the guard and port of FIG. 9 taken on plane 10—10 of FIG. 9.

With particular reference to FIGS. 10A and 10B, port 104 has four internal longitudinally and radially extending ribs 116 that define a pair of channels 118 extending longitudinally between them within which guard 100 can be slidingly guided into port 104 in any one of four orientations so that a respective pair of catches 114 can engage both central recess 101 of guard 100 (see FIG. 9). The inner faces 116a of ribs 116 also serve to guide a phial 118—see FIG. 10B —into port 100, allowing phial 118 to be removed without the danger of the bung 120 of the phial snagging catches 114. In this case, the depth of penetration of the phial and guard 100 are both limited by a set of four short ribs 122 upstanding from the inside of the base of guard 104 and extending inwards of guide ribs 116 (see FIG. 9). Instead of including a pad at the base of port 104, the inner walls of the port and the exposed surfaces of ribs 116 and 122 near the bottom of the port are roughened and/or coated—as indicated at 124— to immobilise any blood or droplets of other liquid that comes into contact therewith. It will be appreciated that, by disposing bottom ribs 112 in between longitudinal guide ribs 116, they will still serve as stops for phial 118 but not as stops for guard 100, so that guard 100 can penetrate to the base of port 104 as in the first example.

The third example is illustrated in FIG. 11 and comprises a tubular needle guard 150 of generally rectangular section and a tubular port 152 of generally circular section. Port 152 includes a cylindrical barrel 154 that has a flanged open end 156 and a closed base 158 having a threaded boss 160 into which the butt of a sampling needle (not shown) can be screwed. In this case, the retaining means comprises a bayonet-type coupling between guard 150 and port 152, guard 150 having a pair of lateral protrusions 162 intermediate of its ends (only one of which is shown in FIG. 11) that can enter corresponding radial slots 164 (only one of which is shown) formed in flange 166 of port 152. Slots 164 allow protrusions 162 to enter a pair of circumferentially extending slots 168 (only one of which is shown) formed in the upper part of the barrel 154 of port 152. A tooth or catch 170 is formed on the underside of flange 166 on each side of slots 164 to retain protrusions 162 against removal, once they have been entered laterally into slots 168 by twisting guard 150 relative to port 152.

FIG. 12 illustrates the fourth example of this invention wherein the retaining means on the guard comprise a pair of laterally-extending and rearwardly-facing teeth or catches 180 formed on the outside of open end 182 of a needle guard 184. Needle guard 184 can be otherwise similar to the guard disclosed in our afore-mentioned prior patents. The coacting retaining means on the corresponding port 186 comprises an indented catch-band 188 formed around barrel 190 of port 186 near its base 192. While guide ribs or slots may be provided on the inside of barrel 190 to separately guide guard 184 and sampling phials (not shown) as in the second example, it is preferred in this case to make the guard and the phials of substantially the same lateral dimension so that they will both slide smoothly into barrel 190 in any angular orientation about their respective longitudinal axes. Conveniently, then, catch-band 188 serves as a stop to limit the inward travel of a phial but allows the open end 182 of guard 184 to be pushed beyond band 188 until teeth 180 are engaged with the band 188. Again, it is desirable that the walls of guard 184 have sufficient flexibility to deform sufficiently to allow teeth 180 to travel beyond catch band 188. In an alternative arrangement, a plurality of small ratchet-like teeth can be formed on the end of guard 184 instead of the single tooth 180 on each side and a series of narrow corresponding catch-bands can be formed in the inside of port barrel 190 instead of the single large band 188.

FIG. 13 illustrates the fifth example, involving a tubular guard 200 and a tubular sampling port 202. In this case, guard 200 is one in which the needle mount (not shown) is captured therein, the IV needle (not shown) being extended from the guard for use and withdrawn back into the guard 200 after use. In this case, guard 200 has an outer dimension that is substantially smaller than the internal diameter of port 202 and the phials (not shown) intended for use in the port.

The retaining means of this example comprise a pair of clips 204 that extend axially from the end face 206 of guard 200 so as to be adapted to engage a plurality of corresponding pairs of membrane-slots 208 formed in the flat base 210 of port 202. Each membrane slot is covered by a thin membrane or 'flash' that can be readily punctured or penetrated by a clip 204. Thus, when guard 200 is pushed right into port 202 and rotated to align clips 204 with a pair of slots 208, it can be pushed a little further to drive clips 204 through slots 208 so that they retain guard 200 in port 202. If desired, at least the end portion of guard 202 may have a rectangular shape (as in the other examples) and port 202 may be provided with internal ribs (as in the second example) so that clips 204 are correctly aligned with a pair of slots 208 as guard 200 is pushed into port 204. This has the advantage of preventing clips 204 being broken off or damaged by excessive pressure before they are aligned with slots 208.

Those skilled in the art will appreciate that many other examples and variations of the application of the principles of the present invention can be made without departing from the scope of the invention as defined in the following claims. For instance, in the example of FIG. 13, clips like those shown on the needle guard (but facing outwardly) can be formed to upstand from the base of the port so as to enter the open end of a guard such as that of the first example and to retain the guard in the port. If desired, a single clip of circular form may be used. In any event, such a clip or clips can also serve to limit the penetration of the phials into the port.

What is claimed is:

1. A method of mitigating the danger of blood-splash contamination from the open end of a tubular needle guard into which a used medical needle has been withdrawn, for mitigating the danger of blood splash from the open end of a tubular sampling port having a used sampling needle mounted therein, or for mitigating the danger needle-stick injury from the sampling needle mounted within the sampling port, the method comprising the step of inserting the open end of the needle guard into the open end of the sampling port.

2. A method according to claim 1 wherein the needle guard is inserted into the sampling port so the sampling needle enters the open end of the guard.

3. A method according to claim 1 including the step of securing the needle guard within the sampling port against unintended removal or separation therefrom.

4. A method according to claim 1 wherein the sampling port has a closed base on which the sampling needle is mounted so as to extend axially into the port, and wherein an adsorbent pad is located within the sampling port against the base so as to surround the sampling needle, the method including the step of inserting the needle guard into the sampling port so that the open end of the needle guard juxtaposes the adsorbent pad.

5. A method according to claim 1 wherein the sampling port has a closed base on which the sampling needle is mounted so as to extend axially into the port, and wherein an adsorbent pad is located within the sampling port against the base so as to surround the sampling needle, the method including the step of:
   inserting a vacuum phial into the port to draw a liquid sample from the sampling needle, said vacuum phial having a bung at one end that is capable of being pierced by the sampling needle,
   ensuring that the phial does not extend into the port sufficiently to allow said bung to contact said pad,
   removing the phial with its sample from the port, and
   inserting the needle guard into the sampling port so that the open end of the needle guard juxtaposes the adsorbent pad.

6. A method of reducing this risk of blood-splash contamination during IV procedures where an IV needle is inserted into a patient or donor and is connected to a tubular sampling port, the sampling port having an open top and a closed base and having a sampling needle is mounted on the base so as to extend into the port for use with evacuated sample phials inserted into the sampling port, the method comprising the steps of:
   withdrawing the IV needle from the patient into a tubular guard through an open end of the guard,
   inserting the guard open-end first into the open top of the sampling port so that the sampling needle enters the open end of the guard, and
   securing the guard within the sampling port against inadvertent removal or separation.

7. Apparatus for use with intravenous (IV) medical procedures comprising:
   an IV needle assembly including a hollow medical needle and a trailing tube in fluid connection with said needle,
   a tubular needle guard having an open end into which the needle can be withdrawn after use so that the needle is shielded by the guard against external contact,
   a tubular sampling port having an open top end, a closed bottom end, a lateral dimension sufficient to permit said needle guard to be slidingly entered into the port open-end-first,
   a hollow sampling needle mounted in said base of the port so as to extend axially into the port, the sampling needle being externally connectable to said trailing tube so that samples of liquid from said tube can be drawn off using the sampling needle, and
   retaining means operable between said guard and said port to retain the guard within the port when the guard is entered into the port open-end-first so that the sampling needle enters the open end of the guard.

8. A tubular needle guard suitable for use with a sampling port in IV procedures, the sampling port having an open top and closed base in which base a sampling needle can be mounted, the needle guard having an open end through which a used hypodermic needle can be withdrawn for shielding within the guard, the needle guard being characterized in that:
   said needle guard is shaped so that said open end can be inserted into the top of sampling port, and
   said needle guard includes retaining means for retaining the needle guard within a sampling port, after insertion into the open top of the sampling port, against subsequent inadvertent removal or disengagement.

9. A needle guard according to claim 8 wherein said retaining means comprises a pawl-like catch on or in said guard adapted to engage a corresponding protrusion or recess formed on or in the sampling port, or wherein said retaining means comprises a protrusion or recess formed on or in the guard adapted to engage a corresponding pawl-like catch on or in the sampling port.

10. A needle guard according to claim 8 wherein said retaining means comprises a laterally extending protrusion or recess on the needle guard adapted for rotary or twisting engagement with a corresponding recess or protrusion is formed on or in the sampling port.

11. A sampling port suitable for use with a needle guard in IV procedures, the needle guard having an open end through which a used hypodermic needle can be withdrawn for shielding within the guard, the sampling port being characterized in that:
   said sampling port has an open top shaped so that the open end of a needle guard can be inserted therein, and
   said sampling port includes retaining means for retaining a needle guard inserted therein against subsequent inadvertent removal or disengagement.

12. A sampling port according to claim 11 wherein said retaining means comprises a pawl-like catch on or in said sampling port adapted to engage a corresponding protrusion or recess formed on or in the guard, or wherein said retaining means comprises a protrusion or recess formed on or in the sampling port adapted to engage a corresponding pawl-like catch on or in the guard.

13. A sampling port according to claim 11 wherein said retaining means comprises a laterally extending recess or protrusion on the sampling port adapted for rotary or twisting engagement with a corresponding protrusion or recess formed on or in the guard.

14. A sampling port according to claim 11 having a tubular body defining said open top, having a closed base and having a sampling needle mounted on the base so as to extend into the body, the sampling port being characterised in that:

stop means are provided therein adapted to limit the depth to which an evacuated sample phial can be entered into the body such that said phial cannot contact the base of the port.

15. A sampling port according to claim 14 wherein said stop means are arranged so as to permit a needle guard to be entered into the port sufficiently to permit contact between the guard and the base of the port.

16. A sampling port according to claim 15 comprising:

first guide means adapted to guide a tubular sampling phial coaxially within the sampling port upon sliding insertion of the sampling phial into the open end of said port, second guide means adapted to guide said needle guard within said body upon sliding insertion of the guard within said port so that the sampling needle enters the open end of the guard, and retaining means associated with said second guide means adapted, upon insertion of the guard into the port to engage the needle guard and to retain said guard within the port against inadvertent removal or separation.

17. A sampling port suitable for use with a needle guard in IV procedures, the needle guard having an open end through which a used hypodermic needle can be withdrawn for shielding within the guard, the sampling port comprising:

a body having a closed base that forms the bottom of the sampling port, a tubular wall with an outwardly flanged open top that forms the open top of the sampling port, and a central axis, means for mounting the sampling needle on or in said base so that the needle projects axially into said body, a first pair of opposed, diametrically spaced and axially extending channels formed in said wall, each channel of said first pair being of outwardly curved section such that a tubular sampling phial of circular section will be axially guided by said channels upon insertion of the phial into the body of the sampling port, said first pair of channels forming said first guide means and the channels of said first pair being diametrically spaced from one another by a first distance, a second pair of opposed, diametrically spaced and axially extending channels formed in said wall in quadrature with said first pair of channels, the channels of said second pair being diametrically spaced from one another by a distance that is greater than said first distance, said channels of the second pair forming said second guide means and being adapted to guide the sides of a needle guard upon insertion of the guard into the body of the sampling port.

18. A sampling port according to claim 11 wherein liquid immobilising means are formed within the port on or near the base thereof.

19. A sampling port according to claim 18 wherein said immobilising means comprises a pad of material that is wettable by said liquid, said pad being located within the sampling-port so as to surround the sampling-port needle on said base.

20. A sampling port according to claim 19 wherein said pad is formed from fibrous porous and liquid adsorbent material.

21. A sampling port according to claim 19 wherein said pad is formed from a synthetic open-cell foamed material.

22. A sampling port according to claim 19 wherein said pad is formed from a porous ceramic material.

23. A sampling port according to claim 18 wherein said immobilising means comprises an area of the internal surface of the sampling-port surrounding the sampling-port needle at or near the base of the sampling-port, said area being coated, treated or roughened so as to promote the adherence of said liquid drops thereto.

24. A sampling port according to claim 18 wherein said immobilising means is adapted to promote rapid clotting of blood.

* * * * *